(12) United States Patent
Bourne et al.

(10) Patent No.: US 7,275,640 B2
(45) Date of Patent: Oct. 2, 2007

(54) PACKAGING FOR IMPARTING ANTI-MICROBIAL PROPERTIES TO A MEDICAL DEVICE

(75) Inventors: George Bourne, Southborough, MA (US); Sally Thornton, Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 374 days.

(21) Appl. No.: 10/772,571

(22) Filed: Feb. 5, 2004

(65) Prior Publication Data

US 2005/0173270 A1 Aug. 11, 2005

(51) Int. Cl.
*B65D 25/08* (2006.01)

(52) U.S. Cl. ............ 206/219; 206/438; 206/568; 220/529

(58) Field of Classification Search ........ 206/219–222, 206/438, 568; 215/DIG. 8; 220/501, 502, 220/529
See application file for complete search history.

(56) References Cited

U.S. PATENT DOCUMENTS

| | | | |
|---|---|---|---|
| 2,157,169 A * | 5/1939 | Foster | 206/222 |
| 3,041,184 A | 6/1962 | Hartshorne | |
| 4,410,321 A | 10/1983 | Pearson et al. | |
| 4,458,733 A | 7/1984 | Lyons | |
| 4,458,811 A | 7/1984 | Wilkinson | |
| 4,463,875 A | 8/1984 | Tepic | |
| 4,484,920 A | 11/1984 | Kaufman et al. | |
| 4,519,499 A | 5/1985 | Stone et al. | |
| 4,533,435 A | 8/1985 | Intilli | |
| 4,637,061 A | 1/1987 | Riese | |
| 4,666,706 A | 5/1987 | Farquharson et al. | |
| 4,678,698 A * | 7/1987 | Mencke | 206/5.1 |
| 4,805,767 A | 2/1989 | Newman | |
| 4,813,210 A | 3/1989 | Masuda et al. | |
| 4,844,259 A | 7/1989 | Glowczewskie, Jr. et al. | |
| 4,851,246 A | 7/1989 | Maxwell et al. | |
| 4,888,175 A | 12/1989 | Burton, Jr. et al. | |
| 4,961,495 A | 10/1990 | Yoshida et al. | |
| 4,994,056 A | 2/1991 | Ikeda | |

(Continued)

FOREIGN PATENT DOCUMENTS

EP 0 378 183 A1 7/1990

(Continued)

OTHER PUBLICATIONS

Hanna, Md, MPH, Hend; Raad, MD, Issam. *New Approaches for Prevention of Intravascular Catheter-Related Infections*, InfectMed 18(1): 38-48; Cliggott Publishing Co. 2001.

(Continued)

*Primary Examiner*—Luan K Bui
(74) *Attorney, Agent, or Firm*—Jones Day

(57) ABSTRACT

Packaging for medical devices that impart anti-microbial properties to the surfaces of a medical device is disclosed. In one embodiment, a first compartment stores a medical device and a second compartment stores an anti-microbial agent. When the medical device is ready to be used, the anti-microbial agent from the second compartment flows into the first compartment to impart anti-microbial properties to the surface of the medical device. In another embodiment, components of the package are treated with an anti-microbial agent, which are then transferred or imparted to the surfaces of a medical device stored within the package.

8 Claims, 7 Drawing Sheets

U.S. PATENT DOCUMENTS

| | | | |
|---|---|---|---|
| 5,114,004 A * | 5/1992 | Isono et al. | 206/222 |
| 5,143,211 A * | 9/1992 | Miczka et al. | 206/221 |
| 5,164,166 A * | 11/1992 | Stepanski et al. | 206/5.1 |
| 5,209,347 A | 5/1993 | Fabisiewicz et al. | |
| 5,242,052 A | 9/1993 | Weder | |
| 5,267,646 A | 12/1993 | Inoue et al. | |
| 5,287,961 A | 2/1994 | Herran | |
| 5,346,061 A | 9/1994 | Newman et al. | |
| 5,370,221 A | 12/1994 | Magnusson et al. | |
| 5,373,966 A | 12/1994 | O'Reilly et al. | |
| 5,398,483 A | 3/1995 | Smith et al. | |
| 5,407,685 A | 4/1995 | Malchesky et al. | |
| 5,423,421 A | 6/1995 | Inoue et al. | |
| 5,462,526 A | 10/1995 | Barney et al. | |
| 5,503,835 A | 4/1996 | Van Roekel | |
| 5,552,968 A * | 9/1996 | Ladyjensky | 206/219 |
| 5,641,496 A | 6/1997 | Van Roekel | |
| 5,706,937 A | 1/1998 | Futagawa et al. | |
| 5,865,309 A | 2/1999 | Futagawa et al. | |
| 5,906,825 A | 5/1999 | Seabrook, Jr. et al. | |
| 5,919,554 A | 7/1999 | Watterson, III et al. | |
| 5,928,213 A | 7/1999 | Barney et al. | |
| 6,186,998 B1 | 2/2001 | Inuzuka et al. | |
| 6,286,670 B1 * | 9/2001 | Smith | 206/221 |
| 6,484,874 B1 | 11/2002 | Kageyama et al. | |
| 6,485,735 B1 | 11/2002 | Steen et al. | |
| 6,517,526 B1 | 2/2003 | Tamari | |
| 6,523,714 B2 | 2/2003 | Serbiak | |
| 6,544,213 B1 | 4/2003 | Lifshey | |
| 6,547,064 B2 | 4/2003 | Klair | |
| 6,641,307 B2 | 11/2003 | Matsuda et al. | |
| 6,648,133 B1 * | 11/2003 | Blaschke et al. | 206/221 |
| 6,838,050 B1 | 1/2005 | Green et al. | |
| 6,966,450 B2 * | 11/2005 | Askew | 220/529 |
| 2002/0049405 A1 | 4/2002 | Deslauriers et al. | |
| 2003/0047467 A1 | 3/2003 | Smith et al. | |
| 2003/0146115 A1 | 8/2003 | Sharp | |
| 2004/0004008 A1 | 1/2004 | Peck et al. | |
| 2004/0004010 A1 | 1/2004 | Versluys | |
| 2004/0010224 A1 | 1/2004 | Bodmeier | |
| 2004/0039366 A1 | 2/2004 | MacLeod | |
| 2004/0045842 A1 | 3/2004 | Matsuda et al. | |

FOREIGN PATENT DOCUMENTS

| | | |
|---|---|---|
| EP | 972506 A2 | 1/2000 |
| EP | 1350739 A2 | 10/2003 |
| WO | WO98/11932 | 3/1998 |
| WO | WO99/65538 | 12/1999 |
| WO | WO 00/47494 | 8/2000 |
| WO | WO 00/74743 | 12/2000 |
| WO | WO 03/092779 A1 | 11/2003 |
| WO | WO 2004/075944 A2 | 9/2004 |
| WO | WO 2004/075944 A3 | 9/2004 |

OTHER PUBLICATIONS

Zhang, Xianping; Whitbourne, Richard; Richmond, Richard D. *Antiinfective Coatings for Indwelling Medical Devices*, Nov./Dec. 1997.

"Infection Control and Biosafety: Trends, Products and Opportunities," Medical Data Informational Report, Irving, CA, MDI, 1:33-44, 1993.

* cited by examiner

PACKAGING FOR IMPARTING ANTI-MICROBIAL PROPERTIES TO A MEDICAL DEVICE

FIELD OF THE INVENTION

This invention is generally directed to the imparting of anti-microbial properties to medical devices, and more particularly to the use of medical device packaging as a way to impart anti-microbial properties to medical devices.

BACKGROUND OF THE INVENTION

Despite the advances in sterilization, infections resulting from the use of medical devices continue to pose a problem. Even if a medical device has been properly sterilized before use, mere sterilization does not prevent a medical device from subsequently becoming re-contaminated by disease-causing microbes. For example, the surface of medical devices, such as catheters, that remain partially implanted within the body can become re-contaminated after the initial implantation by infectious microbes that travel through the air. The microbes can then grow on the surface of the medical device and eventually enter the body through the entry site of the medical device into the body, resulting in infection. Re-sterilization of the device after implantation, even when feasible, is difficult and time-consuming.

Therefore, it has been found that in addition to sterilizing medical devices before use, it is desirable to also impart anti-microbial properties to the surface of the medical devices, particularly for those medical devices, such as catheters, that remain partially inserted in the body for a substantial period of time. By preventing the growth of microbes on the surface of medical devices after implantation, infections may be further reduced.

Providing the surfaces of medical devices with anti-microbial properties is known in the art. Current methods used to impart anti-microbial agents onto medical devices included coating or co-extruding the surface of the medical device with an anti-microbial agent. However, these methods often require a change in the manufacturing process of the medical device, which may be difficult, costly and/or impractical. Furthermore, if the medical device is to be stored for a long time prior to use, there may be a degradation of the effectiveness of an anti-microbial coating on the medical device.

The present invention teaches a novel method of imparting anti-microbial agents onto medical devices by using certain packaging advantages.

SUMMARY OF THE INVENTION

In a first embodiment, a system for packaging a medical device comprises a container with a first compartment and a second compartment, the first compartment being configured and adapted to house the medical device, and the second compartment being configured and adapted for containing an anti-microbial agent. A partition between the first compartment and the second compartment prevents fluid communication between the first compartment and the second compartment, with at least part of the partition being removable or breakable to allow fluid communication between the first compartment and the second compartment.

In a further embodiment, the partition further comprises an opening and a sealing element covering said opening. The sealing element may be removable from the opening. The sealing elements may be removed by peeling the sealing element from the opening. Alternatively, the partition may further comprise a removable member attached to the partition, wherein removal of the removable member results in a tearing of the partition.

In yet another embodiment, a cover is capable of being disposed over the container. The removable or breakable part of the partition may be connected to the cover.

The anti-microbial agent may be selected from iodine, hypohalites, haloamines, thiocyanogen, hypothiocyanite, silver ions, triclosan, penicillin, amoxycillan, rapromycin, or combinations thereof. The anti-microbial agent may be a fluid or a gel.

In another preferred embodiment of the present invention, a method for imparting anti-microbial properties to a medical device comprises the steps of (a) obtaining a container comprising a sealable first compartment configured and adapted to house the medical device, a sealable second compartment configured and adapted to store an anti-microbial agent, and a partition between the first compartment and the second compartment to prevent fluid communication between the first compartment and the second compartment, wherein at least part of the partition being breakable or removable to allow fluid communication between the first compartment and the second compartment; (b) filling the second compartment with an anti-microbial agent; (c) placing a medical device in the first compartment; (d) sealing the first and second compartments; and (e) removing or breaking at least part of the partition to allow fluid communication between the first and the second compartments to allow the anti-microbial agent to flow from the second compartment into the first compartment. The method may further comprise allowing the anti-microbial agent to coat the medical device.

In a further embodiment, the container further comprises a cover capable of being disposed over the container, and the removable or breakable part of the partition is connected to the cover; and the step of removing the removable part of the partition is accomplished by removing the cover from the container.

In another preferred embodiment, the system for packaging a medical device having a lumen, comprises a pouch comprising an interior surface and a first anti-microbial agent; a tray disposed within the pouch; and a substrate attached to the tray; wherein the substrate comprises a second anti-microbial agent and wherein the substrate is capable of being inserted into the lumen. The first anti-microbial agent may be disposed on the interior surface of the pouch. In a preferred embodiment, the substrate is in the form of a rod, and may be formed of an iodine-polycarbonate material. In another preferred embodiment, the substrate may be coated with the second anti-microbial agent. The first and the second anti-microbial agents may be the same. The pouch may further comprise a sealable opening.

In a further embodiment, the system further comprises a cylinder comprising a third anti-microbial agent, wherein the cylinder is disposed around the tray and within the pouch. The third anti-microbial agent may be the same as the first and second anti-microbial agents. The cylinder may be formed from the third anti-microbial agent. In another preferred embodiment, the third anti-microbial agent is coated onto the cylinder.

In another preferred method for imparting anti-microbial properties to a medical device having a lumen, the method may comprise the steps of (a) obtaining a container comprising a pouch having an interior surface, a tray disposed within the pouch, and a substrate attached to the tray, wherein the interior surface of the pouch comprises a first anti-microbial agent, and the substrate comprises a second anti-microbial agent; (b) inserting the substrate into the lumen; and (c) inserting the tray in to the pouch. The method may further comprise the step of sealing the pouch. The lumen may be filled with an aqueous solution, wherein the aqueous solution serves as a release medium for the second anti-microbial agent. The first and the second anti-microbial agents may be the same.

The present invention allows for the imparting of anti-microbial agents to medical devices without otherwise changing the characteristics or materials of the medical devices. Furthermore, the present invention allows anti-microbial agents to be imparted to medical devices without changing the manufacturing process for the medical device. Also, the present invention allows the anti-microbial agent to be imparted to the medical device shortly before used of the medical device, thereby avoiding potential degradation of the effectiveness of the anti-microbial agent.

BRIEF DESCRIPTION OF THE DRAWINGS

FIG. 2A illustrates a zip strip secured to the partition, while FIG. 2B illustrates the zip-strip being partially removed from the partition.

FIG. 3A illustrates the zip strip secured to the partition, while FIG. 3B illustrates the zip-strip that is attached to a portion of the partition being partially torn away from the remainder of the partition.

DETAILED DESCRIPTION OF THE PREFERRED EMBODIMENT

Figure 1:
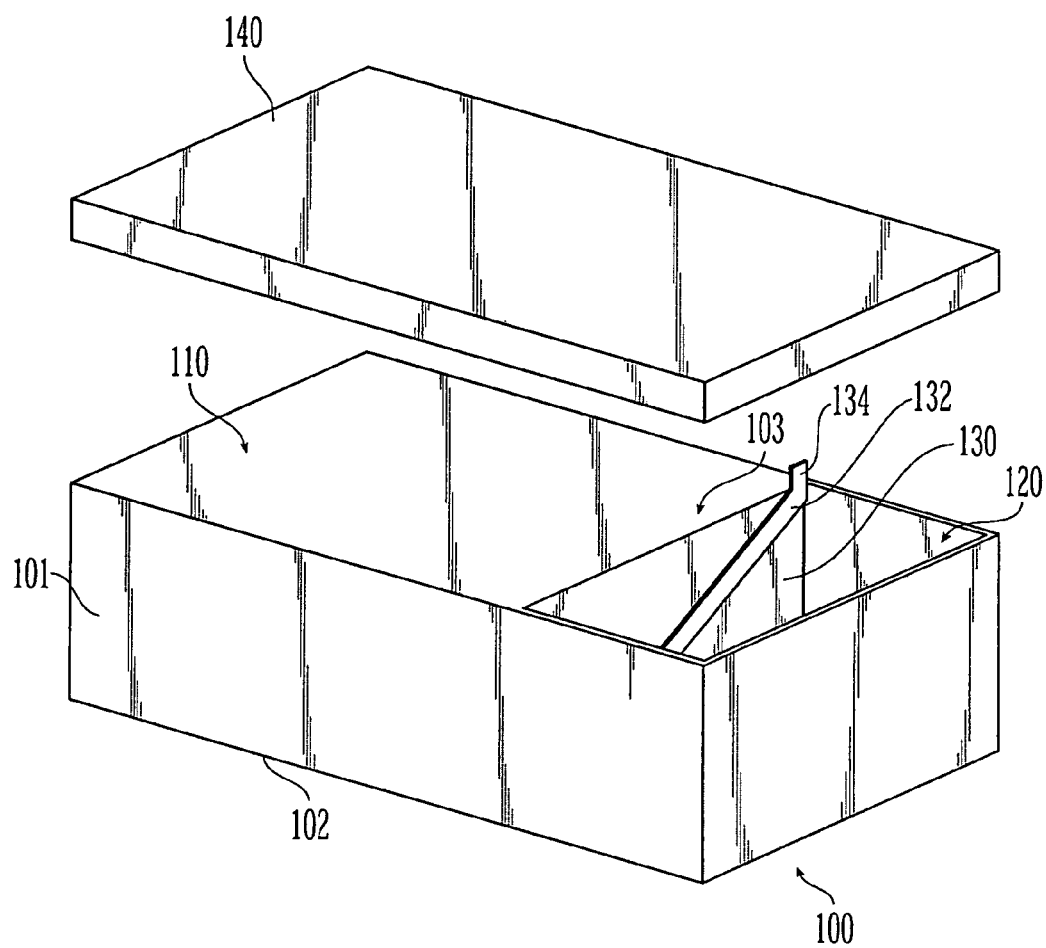
FIG. 1 is a perspective view of an embodiment of the present invention with the cover removed.
Figure 2:
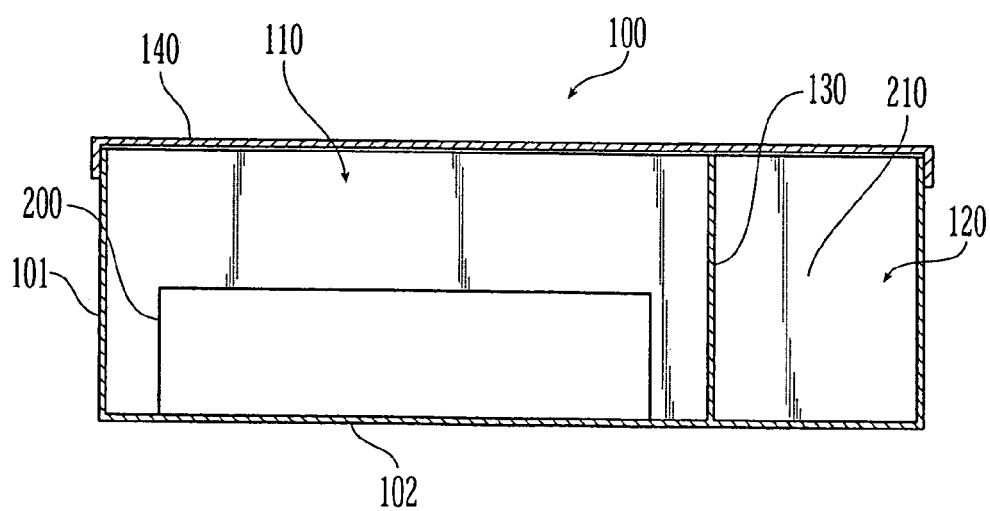
FIG. 2 is a cross-sectional view of the embodiment of FIG. 1.

In a preferred embodiment, as shown in FIGS. 1 and 2, package 100 generally comprises container 101 with bottom 102, open top 103, and removable cover 140 that is capable of being disposed over the container. Partition 130 separates the interior of container 101 into first compartment 110 and second compartment 120. The partition 130 prevents the first compartment from being in fluid communication with the second compartment. First compartment 110 is configured and adapted to hold medical device 200. Second compartment 120 is configured and adapted to hold an anti-microbial agent 210.

Container 101 may be made of various materials. Suitable materials include without limitation polyurethane and its copolymers, silicone and its copolymers, ethylene vinyl-acetate, polyethylene terephthalate, thermoplastic elastomers, polyvinyl chloride, polyolefins, cellulosics, polyamides, polyesters, polysulfones, polytetrafluoroethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins. Preferred materials include, but are not limited to, polyethylene terephthalate, polypropylene, polystyrene, polyethylene, and polyurethane.

The partition can be made of material that is the same as or different from the container material. Preferably the material used to make the partition is a polymeric material.

Suitable anti-microbial agents include, but are not limited to, elemental iodine (also called free iodine), hypohalites, haloamines, thiocyanogen, hypothiocyanite, silver ions, triclosan, antibiotics such as penicillin and amoxycillan, and rapromycin. Preferably the anti-microbial agent 210 is in gel or fluid or liquid form. Agent 210 may also be in a gaseous form.

Figure 2A:
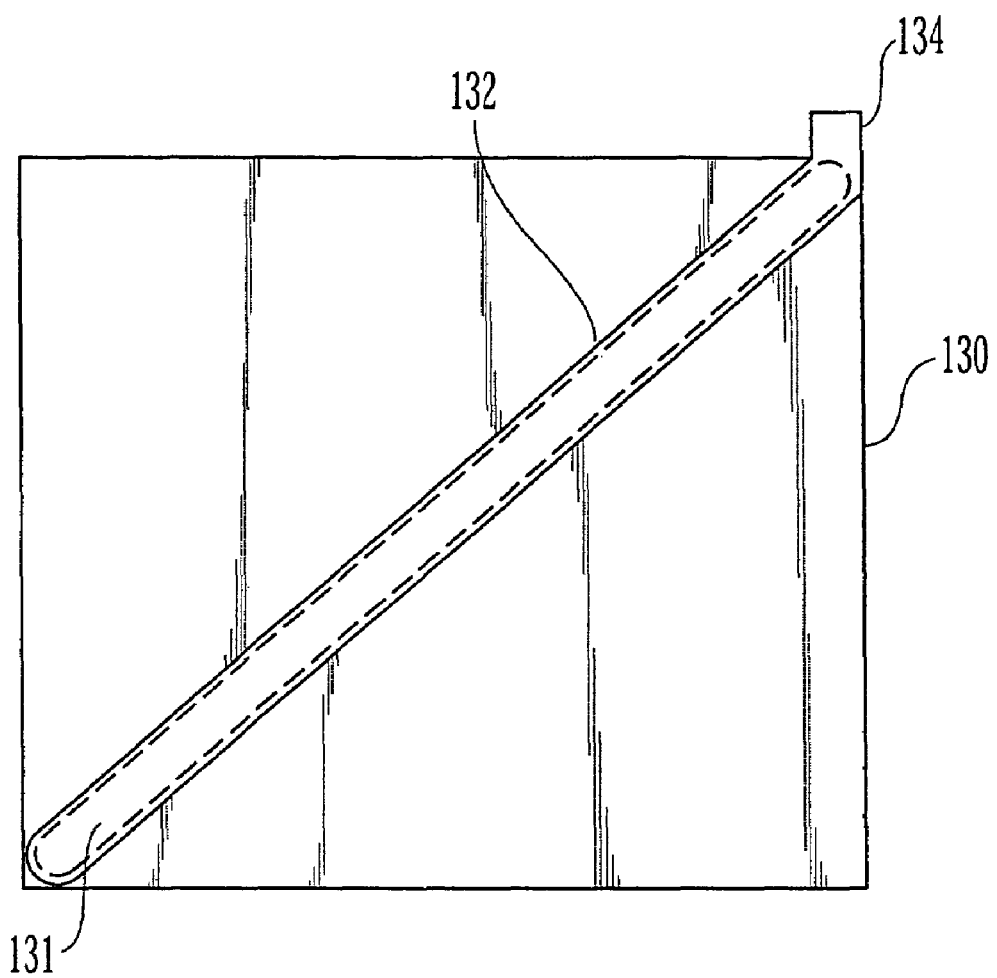
FIGS. 2A and 2B are side views of the partition of the embodiment of FIG. 1.

Partition 130 separates first compartment 110 and second compartment 120. When partition 130 is broken or removed, first compartment 110 and second compartment 120 are in fluid-communication with one another. In a preferred embodiment, partition 130 is formed with partition opening 131 (as shown in FIG. 2A), which is sealed or covered by removable sealing member or "zip-strip" 132. Removal of zip-strip 132 allows anti-microbial agent 210 to flow from second compartment 120 into first compartment 110 through opening 131. Zip strip 132 may be removed by peeling it from partition 130. In the embodiment shown in FIG. 2B, opening 132 is a slit that is formed along a diagonal of partition 130. However, opening 132 may take on many different configurations and still be within the spirit and scope of the invention. Preferably, opening 131 is configured such that at least a portion of partition wall 130 near bottom 102 will be compromised when zip-strip 132 is removed, to allow for all of anti-microbial agent 210 to flow from second compartment 120 to first compartment 110. Therefore, it is preferable that opening 131 ends at or proximate to the bottom 131 of container 101.

Figure 2B:
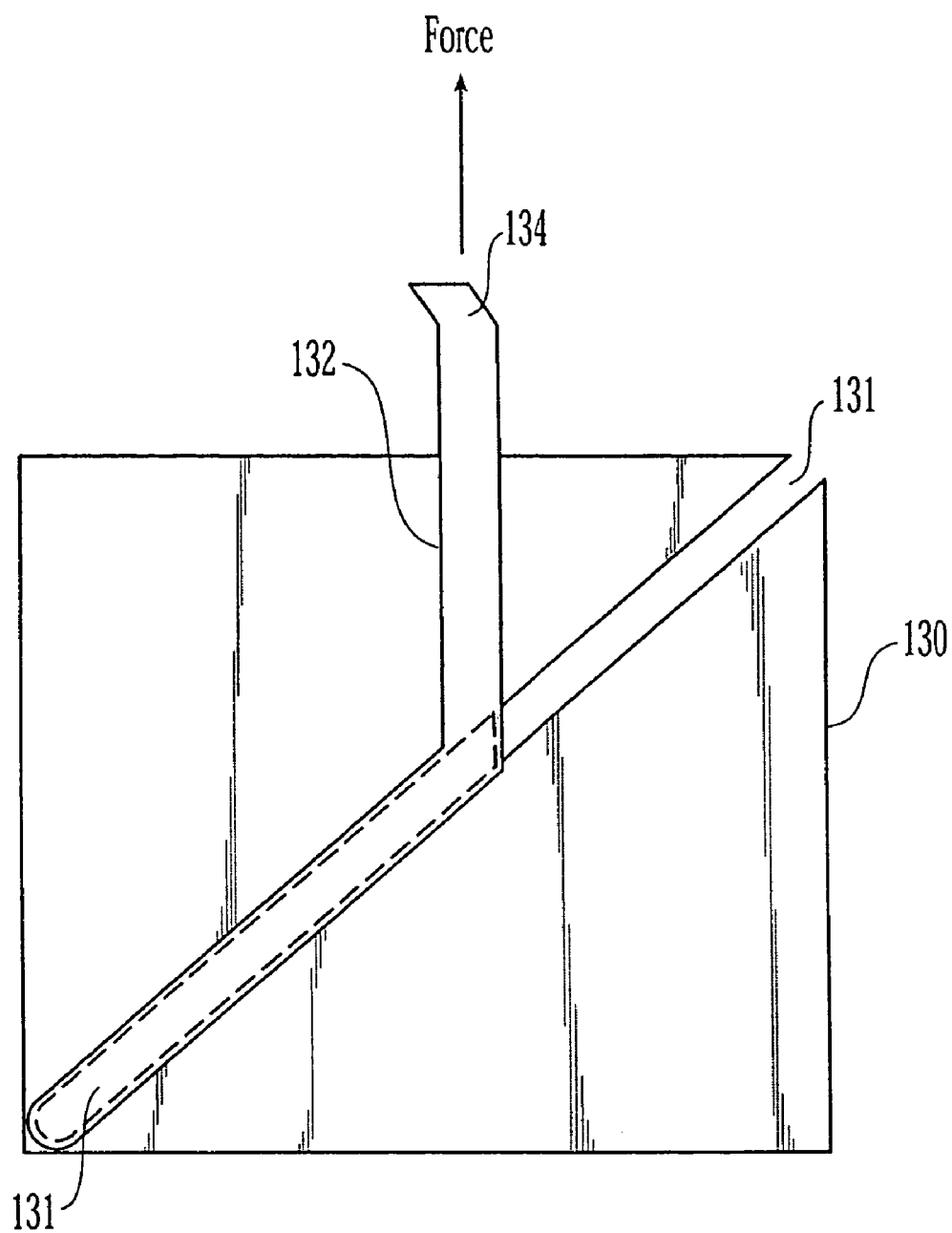

Zip strip 132 may be connected to cover 140 by attaching tab 134 to cover 140. In this configuration, removal of cover 140 from container 101 will simultaneously remove zip-strip 132 from opening 131 (as shown in FIG. 2B). The skilled artisan is aware of methods suitable for attaching tab 134 to cover 140.

Figure 3A:
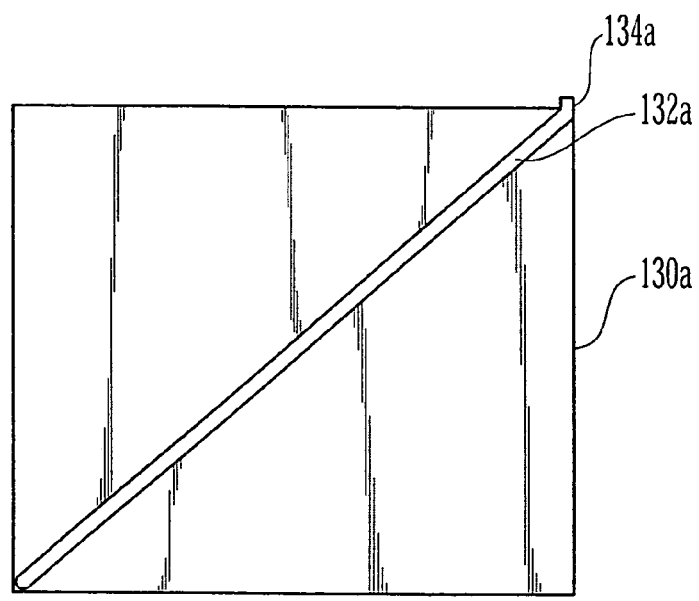
FIGS. 3A and 3b are side views of another embodiment of a zip strip and a partition.
Figure 3B:
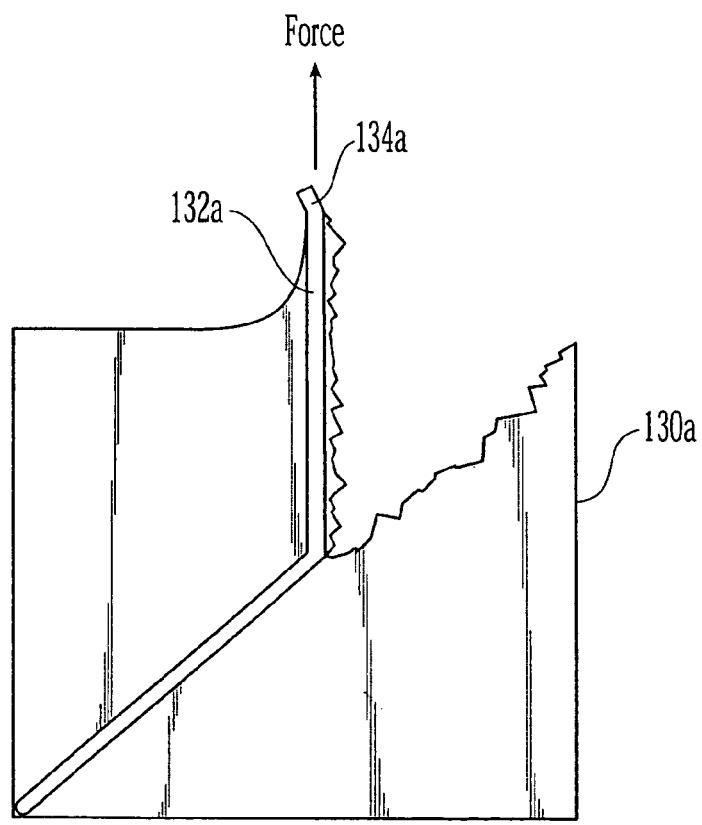

It is readily seen that the invention may be practiced by several different configurations of the partition 130 and zip-strip 132, so long as the removal of zip strip 132 results in fluid- or flow-communication being established between first compartment 110 and second compartment 120. For example, in an alternative embodiment, as shown in FIGS. 3A and 3B, partition 130a does not have an opening, but rather is composed of a material that is easily breakable or torn. Zip strip 132a is adhesively attached to partition 130a. Removal of zip strip 132a by pulling on tab 134a results in the tearing of partition 130a, thus establishing flow-communication between first compartment 110 and second compartment 120. Preferably, in this embodiment zip-strip 132a is more resistant to tearing than partition 130a, so that zip-strip 132a will not break as partition 130a is being torn.

Package 100 is prepared for use by first sterilizing first and second compartments 110 and 120 of container 101. Second compartment 120 is then filled with anti-microbial agent 210, and medical device 200 is placed into first compartment 110. Cover 140 is then placed over the top of container 101 and partition wall 130, sealing first compartment 110 and second compartment 120. In certain embodiments, tab 134 of zip-strip 132 is attached or connected to cover 140. Preferably, cover 140 is attached to container 101 so that first compartment 110 and second compartment 120 are hermetically sealed, to prevent microbes from entering and contaminating medical device 200 and/or exposing anti-microbial agent 210 to the environment, which may cause degradation of the effectiveness of anti-microbial agent 210. Package 100 may then be stored until medical device 200 is needed.

When medical device 200 is needed, the user opens container 101 by removing cover 140. Zip-strip 132, if attached to cover 140, is simultaneously removed from opening 131. Otherwise, zip-strip 132 is removed after cover 140 is removed. Second compartment 120 and first compartment 110 are now in fluid- or flow-communication with each other through opening 131, allowing anti-microbial agent 210 to flow from second compartment 120 into first compartment 110 to impart anti-microbial properties to the surface of medical device 200. Preferably, the anti-microbial agent coates or bathes the medical device. Once a sufficient amount of time has elapsed, the user may then remove medical device 200 from first compartment 110. To ensure that all parts of medical device 200 are exposed to the anti-microbial agent 210 and to facilitate the flow of anti-microbial agent 200 from second compartment 120 to first compartment 110, the user may shake or tilt container 101 accordingly.

It is readily appreciated that medical device 200 does not have to be modified in any way in order to be stored within packaging embodying the present invention. Thus, anti-microbial properties may be provided to medical device 200 without modifying medical device 200 or its manufacturing process.

Packaging that embodies the present invention is preferable to having an anti-microbial agent that is stored and applied separately by the user. For instance, by connecting zip-strip 132 to cover 140, exposure of the medical device 200 to the anti-microbial agent 210 occurs automatically once cover 140 is removed from container 101, providing a safeguard against inadvertently forgetting to treat medical device 200 with anti-microbial agent 210. Because a sufficient amount of anti-microbial agent 210 is packaged with medical device 200, the danger of using too little or too much of anti-microbial agent 210 is also minimized. Furthermore, because anti-microbial agent 210 is stored in a hermetic environment, any environmentally caused degradation of the anti-microbial agent is reduced.

Another advantage is that one anti-microbial agent 210 is readily interchangeable with other anti-microbial agents, even if their physical properties, such as weight and viscosity, differed greatly. Thus, the potential difficulties of modifying a manufacturing technique for a medical device are avoided.

Many modifications and alternative embodiments of the above concepts may be utilized while remaining within the spirit and scope of the present invention. For example, in another preferred embodiment, zip strip 132 is not attached to cover 140 by tab 134. This embodiment allows the user to delay the exposure of the medical device to the anti-microbial agent until after the cover has been opened. In yet another preferred embodiment, separate covers may be provided for first compartment 110 and second compartment 120. This embodiment allows anti-microbial agent 210 and medical device 200 to be sealed into their respective compartments at different times in the manufacturing/packaging process.

Figure 4:
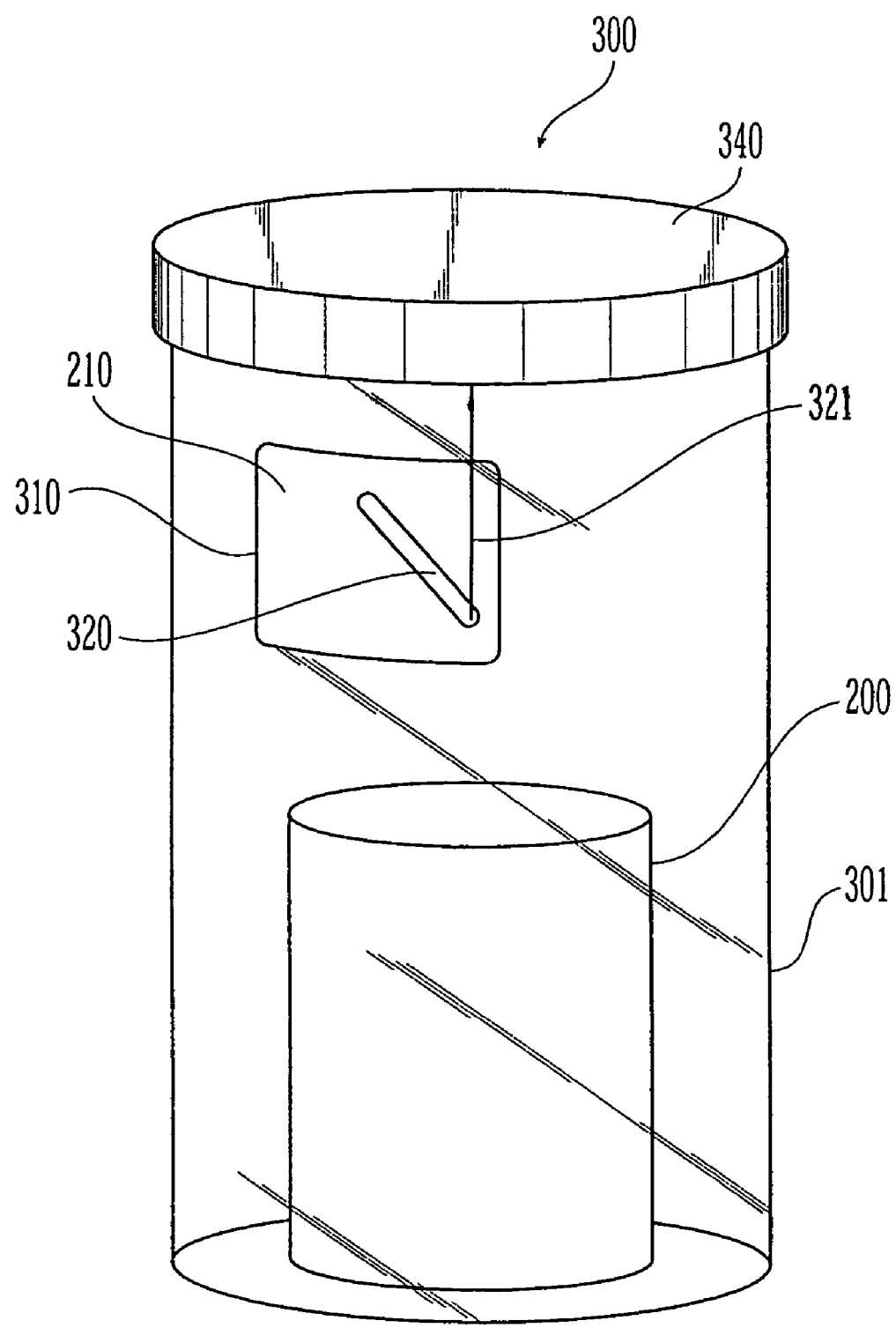
FIG. 4 is a perspective view of another embodiment of the present invention.

Furthermore, many different configurations of the container and the two compartments may be used within the spirit and scope of the present invention. For example, in the preferred embodiment illustrated in FIG. 4, container 301 is generally in the form of a tube which is configured and adapted to house medical device 200. Attached to the top of container 301 is a compartment for housing the anti-microbial agent that is in the form of a gel-pack 310, which is composed of a readily torn material. The gel pack 310 is filled with anti-microbial agent 210 and is situated directly over medical device 200. The zip strip 320 is attached to the gel pack 310 and to the cover 340 via a string 321. Removal of cover 340 from container 301 tears zip strip 320 from gel pack 310, opening gel pack 310 and allowing anti-microbial agent 210 to spill onto medical device 200. Alternatively, the zip-strip may not be attached to the cover, so that the cover must first be removed before the zip-strip is removed.

Medical device 200 may be any of a number of devices, including scalpels, retractors, clamps, catheters, suture needles, and other medical devices.

Another method of using packaging to impart anti-microbial properties to a medical device is to treat components of the packaging with anti-microbial agents. The components of the packaging would then transfer the anti-microbial agents to the medical device, preferably via diffusion.

Figure 5:
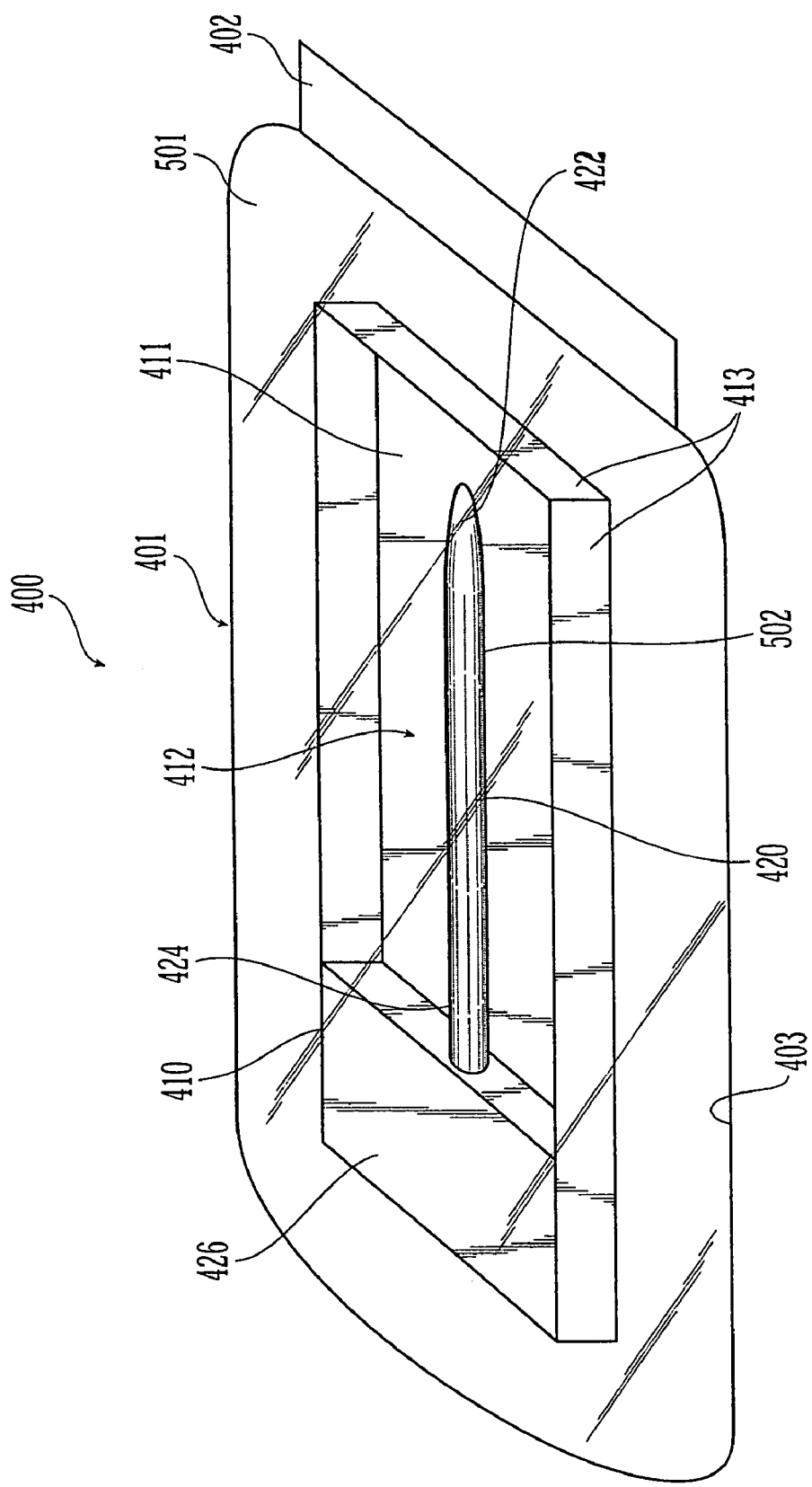
FIG. 5 is a perspective view of yet another embodiment of the present invention.

FIG. 5 illustrates a preferred embodiment of the present invention. Package 400 comprises a pouch 401 and a tray 410. Pouch 401 further comprises sealable opening 402 and interior surface 403. Interior surface 403 is treated with a first anti-microbial agent 501. This can be accomplished in a number of ways. For example, interior surface 403 may be coated with first anti-microbial agent 501. Interior surface 403 may also have first anti-microbial agent 501 embedded within it. First anti-microbial agent 501 may also be integrally mixed into the material that composes interior surface 403.

Suitable anti-microbial agents include, but are not limited to, elemental iodine (also called free iodine), hypohalites, haloamines, thiocyanogen, hypothiocyanite, silver ions, triclosan, antibiotics such as penicillin and amoxycillan, and rapromycin.

Tray 410 generally comprises bottom 411, open top 412, tray walls 413, and substrate 420. Substrate 420 has distal end 422 and proximal end, 424 and is attached to base 426. Base 426 is attached to tray 410. In a preferred embodiment, base 426 is removable from tray 410. Substrate 420 is configured and adapted to fit inside medical device 200 with interior surfaces that may be exposed to a patient, e.g., a lumen of a medical device. For example, medical device 200 may be a catheter with a lumen, and substrate 420 may be in the form of a rod that is insertable into the lumen.

It is preferred that pouch 401 is manufactured from a material that can prevent the migration of iodine or other anti-microbial agents through pouch 401. Suitable materials include without limitation polyurethane and its copolymers, silicone and its copolymers, ethylene vinyl-acetate, polyethylene terephthalate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins. Preferred materials include, but are not limited to, polyethylene terephthalate, polypropylene, polystyrene, polyethylene, and polyurethane.

Substrate 420 can be formed from a second anti-microbial agent 502 that may be the same or different from the first anti-microbial agent 501. In a preferred embodiment, substrate 420 may be made of an iodine-polycarbonate material. Alternatively, the substrate 420 can be formed from a material that does not contain an anti-microbial agent. The anti-microbial agent is then coated onto the substrate. For example, suitable materials for forming the substrate include a polymer that is biodegradable or non-biodegradable. In addition, the polymer that may be hydrophilic or hydrophobic, and may be selected from the group of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example.

Preferred materials for the substrate 420 include, but are not limited to, polyurethane, polycarbonate, silicone, ethyl vinyl acetate, polypropylene, polyamides, polyimides, PEBAX or similar material, and co-polymers thereof. The material may be biodegradable or non-biodegradable.

The amount of second anti-microbial agent 502 may be varied according to the desired effect. The manufacture of the substrate 420 and the use of the substrate 420 for providing anti-microbial activity is described in WO 00/74743 A1.

An aqueous solution may also be contained in the lumen of the catheter or medical device 200. The aqueous solution may be any solution that can serve as a release medium for the second anti-microbial agent 502 from the substrate. Suitable solutions include, but are not limited to, saline, heparin, and sterile water. Once the substrate 420 is positioned in the lumen, the substrate 420 is exposed to the aqueous solution. The aqueous solution allows the second anti-microbial agent 502, such as iodine, to migrate from the substrate 420 and enter the liquid phase. By egressing from the substrate 420 and entering the liquid phase in the aqueous solution, second anti-microbial agent 502 can proliferate along the entire length of the lumen to provide anti-infection activity. The lumen does not have to contain an aqueous solution, in which case the second anti-microbial agent 502 would egress from the substrate 420 and impart anti-microbial properties to the lumen of the medical device 200.

Medical device 200, after being sterilized, is placed in tray 410, with substrate 420 being inserted into a lumen or other interior compartment of medical device 200 that is to be treated. Tray 410 is then inserted into pouch 401 and opening 402 is sealed. Second anti-microbial agent 502 is released from interior surface 403 and substrate 420 onto the exterior and interior surfaces of medical device 200 respectively. It is readily seen that no modifications of medical device 200 need to be made.

It is noted that certain types of anti-microbial agents may need humidity and/or elevated temperatures within package 400 to facilitate diffusion of the anti-microbial agent onto the surface of medical device 200.

Figure 6:
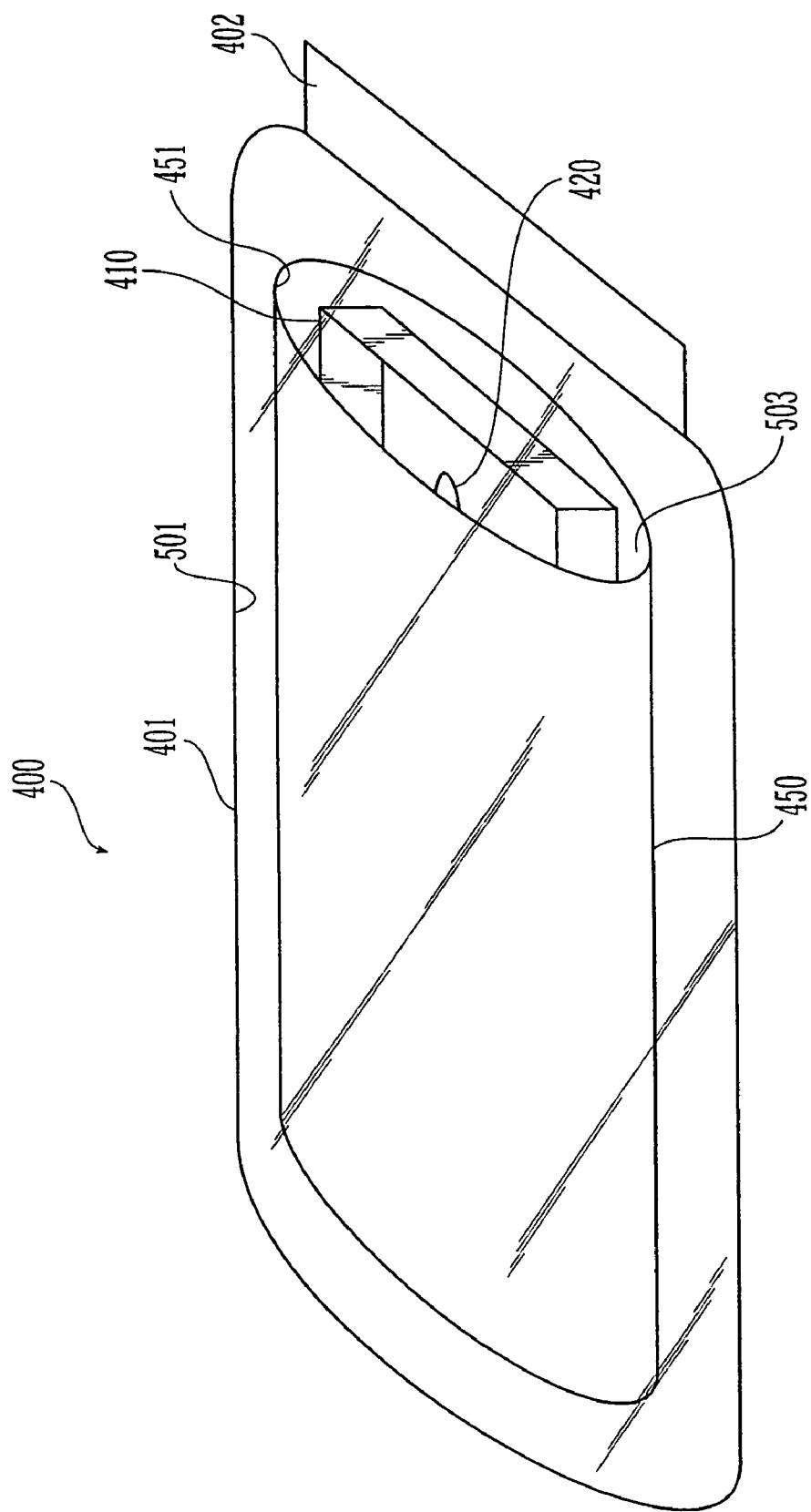
FIG. 6 is a perspective view of yet a further embodiment of the present invention.

In an alternative embodiment, as shown in FIG. 6, package comprises pouch 400, cylinder 450, and tray 410. In this embodiment, interior surface 451 of cylinder 450 is treated with a third anti-microbial agent 503 instead of or in addition to interior surface 403 of pouch 401. This embodiment may be used if there is difficulty in providing the interior surface 403 of pouch 401 with anti-microbial agent 501. It may be easier to provide interior surface 451 of cylinder 450 with third anti-microbial agent 503, as cylinder 450 may be composed of the same material as rod 410. In this embodiment, substrate 420 is inserted into medical device 200, and then tray is inserted into cylinder 450. Cylinder 450 and tray 410 are then sealed within pouch 401. Substrate 420 imparts the second anti-microbial agent 502 to the interior surfaces of medical device 200, while cylinder 450 imparts third anti-microbial agent 503 to the exterior surfaces of medical device 200. The first, second, or third anti-microbial agents may be the same or different.

It is readily seen that many different modifications can be made to the package as described above without departing from the spirit and scope of the present invention. For example, multiple rods may be provided to treat the interior surfaces of a medical device with multiple lumens or interior compartments. Instead of a pouch made of a flexible material, a container made of a rigid material may be used. All references cited herein are incorporated by reference in their entirety for all purposes.

What is claimed:

1. A system for packaging a medical device, comprising:
   a container with a first compartment and a second compartment, the first compartment housing the medical device, and the second compartment containing an anti-microbial agent; and
   a partition between the first compartment and the second compartment to prevent fluid communication between the first compartment and the second compartment, at least part of the partition being removable or breakable to allow fluid communication between the first compartment and the second compartment;
   wherein the partition further comprises an opening and a sealing element covering said opening.

2. The system of claim 1, wherein the sealing element is removable from the opening.

3. The system of claim 2, wherein the sealing elements is removable by peeling the sealing element from the opening.

4. The system of claim 1, further comprising a cover that is capable of being disposed over said container.

5. The system of claim 4, wherein the removable or breakable part of the partition is connected to the cover.

6. The system of claim 1, wherein the anti-microbial agent is selected from iodine, hypohalites, haloamines, thiocyanogen, hypothiocyanite, silver ions, triclosan, penicillin, amoxycillan, rapromycin, or combinations thereof.

7. The system of claim 1, wherein the anti-microbial agent is a fluid.

8. The system of claim 1, wherein the anti-microbial agent is a gel.

* * * * *

UNITED STATES PATENT AND TRADEMARK OFFICE
CERTIFICATE OF CORRECTION

| | | |
|---|---|---|
| PATENT NO. | : 7,275,640 B2 | Page 1 of 1 |
| APPLICATION NO. | : 10/772571 | |
| DATED | : October 2, 2007 | |
| INVENTOR(S) | : George Bourne and Sally Thornton | |

It is certified that error appears in the above-identified patent and that said Letters Patent is hereby corrected as shown below:

In claim 3, col. 8, line 49, "elements" should be --element--

Signed and Sealed this

Thirteenth Day of May, 2008

JON W. DUDAS
*Director of the United States Patent and Trademark Office*